United States Patent
Platica

(10) Patent No.: US 6,656,686 B2
(45) Date of Patent: Dec. 2, 2003

(54) METHOD OF SIMULTANEOUS DETECTION OF BASE CHANGES (SDBC) IN EXPRESSED GENES

(76) Inventor: Ovidiu Platica, 315 E. 65$^{th}$ St., Apt. 11B, New York, NY (US) 10021

( * ) Notice: Subject to any disclaimer, the term of this patent is extended or adjusted under 35 U.S.C. 154(b) by 0 days.

(21) Appl. No.: 09/808,504

(22) Filed: Mar. 14, 2001

(65) Prior Publication Data

US 2002/0072057 A1 Jun. 13, 2002

Related U.S. Application Data

(60) Provisional application No. 60/190,879, filed on Mar. 21, 2000, and provisional application No. 60/266,191, filed on Feb. 2, 2001.

(51) Int. Cl.$^7$ .......................... C12Q 1/68; C07H 21/02; C07H 21/04; C12N 15/00
(52) U.S. Cl. .................. 435/6; 536/23.1; 536/24.3; 935/76; 935/77; 935/78
(58) Field of Search ............................ 435/6; 536/23.1, 536/24.3

(56) References Cited

U.S. PATENT DOCUMENTS

| | | | |
|---|---|---|---|
| 5,589,329 A | * | 12/1996 | Winkler et al. |
| 5,851,770 A | * | 12/1998 | Babon et al. |
| 5,869,245 A | * | 2/1999 | Yeung |
| 5,874,212 A | * | 2/1999 | Prockop et al. |
| 5,958,692 A | * | 9/1999 | Cotton et al. |

OTHER PUBLICATIONS

Borresen, A.L., E. Hove, B. Smith–Sorenssen, D. Malkin, S. Lystad, T.I. Andersen, J.M. Nesland, K.H. Isselbacher, and S.H. Friend. 1991. Constant denaturant gel electrophoresis as a rapid screening technique for p53 mutations. Proc. Natl. Acad. Sci. 88:8405–8409.

Chee, M., R. Yang, E. Hubbell, A. Berno, S.C. Huang, D. Stern, J. Winkler, D.J. Lockhart, M.S. Morris, and S.P. Fodor. 1996. Accessing genetic information with high density DNA arrays. Science 274:610–614.

Chomszynski, P., and Sacchi, N., 1987. Single step method of RNA isolation by acid guanidinium thiocyanate phenol chloroform extraction. Anal. Biochem. 162:156–159.

Cotton, R.G., N.R. Rodriguez, and Campbell. 1988. Reactivity of cytosine and thymine in single base pair mismatches with hydroxylamine and osmium tetroxide and its application to the study of mutations. Proc. Natl. Acad. Sci.. 85:4397–4401.

Cooper, D.N., B. A. Smith, H.J. Cooke, S. Niemann, and J. Schmidtke. 1985 An estimate of unique DNA sequence heterozygosity in the human genome. Hum. Genet. 69:201–295.

Donis–Keller H. 1979. Site specific enzymatic cleavage of RNA. Nucl. Acids Res. 7: 179–192.

Faham, M., and D.R. Cox. 1996. A novel in vivo method to detect DNA sequence variation. Genome Res. 5:474–482.

Fisher, S.G., and L.S. Lerman. 1983. DNA fragments differing by single base pair substitutions are separated in denaturing gradient gels. Correspondence with melting theory. Proc. Natl. Acad. Sci. 80: 1579–1583.

Goodwin E. C. and F.M. Rottman 1991. The use of Rnase H and poly(A) junction oligonucleotides in the analysis of in vitro polyadenylation reaction products. Nucl. Acids Res. 20: 916.

Hacia JG, Brody LC, Chee MS, Fodor SP, Collins FS. 1996. Detection of heterozygous mutations in BRCA1 using high density oligonucleotide arrays and two–colour fluorescence analysis. Nat Genet. 14(4):441–7.

Kwok, P.Y., C. Carlson, T. D. Yager, W. Ankener, and D. A. Nickerson. 1994. Comparative analysis of human DNA variations by fluorescence based sequencing of PCR products. Genomics 23: 138–144.

Liu, Q. and S.S. Sommer. 1995. Restriction endonuclease fingerprinting (REF): A sensitive method for screening mutations in long, contiguous segments of DNA. BioTechniques 18:470–477.

Lu, A.–L. and I.C. Hsu. 1991. Detection of single DNA base mutations with mismatch repair enzymes. Genomics 14:249–255.

Meador J., B. Cannon, V. J. Cannistraro and D. Kennell 1989. Purification and characterization of *E. coli* Rnase I. Eur. J. Biochem., 187: 549–543.

Myers, R.M., Z. Larin, and T. Maniatis. 1985. Detection of single base substitutions by ribonuclease cleavage of mismatches in RNA:DNA duplexes. Science 230:1242–1246.

Myers. R.M., Ellenson L.H. and K. Hayashy. Detection of DNA variation in Genome Analysis, Cold Spring Laboratories Press, vol. 2, pp. 287–379.

Novack, D.F., N.J. Casna, S.G. Fischer, and J.P. Ford. 1986. Detection of single base pair mismatches in DNA by chemical modification followed by electrophoresis in 15% polyacrylamide gel. Proc. Natl. Acad. Sci. 83:586–590.

(List continued on next page.)

Primary Examiner—Ethan Whisenant
(74) Attorney, Agent, or Firm—Pennie & Edmonds LLP

(57) ABSTRACT

This invention is directed to a method for detecting base changes in a nucleic acid of interest which comprise the following steps: (a) contacting the nucleic acid of interest with a suitable reference nucleic acid under suitable conditions that the nucleic acid of interest forms a heteroduplex with the reference nucleic acid; (b) contacting the heteroduplex with a combination of suitable nucleases so as to selectively cleave the heteroduplex if a base change(s) is present; (c) ligating a detectable probe to the cleaved heteroduplex; and (d) detecting the ligated probe under suitable conditions so as determine the location and the sequence of the base changes. The invention also includes kits for practicing the method. Also included are methods of identifying polymophisms associated with particular cancers.

11 Claims, 3 Drawing Sheets

OTHER PUBLICATIONS

Figure 1:
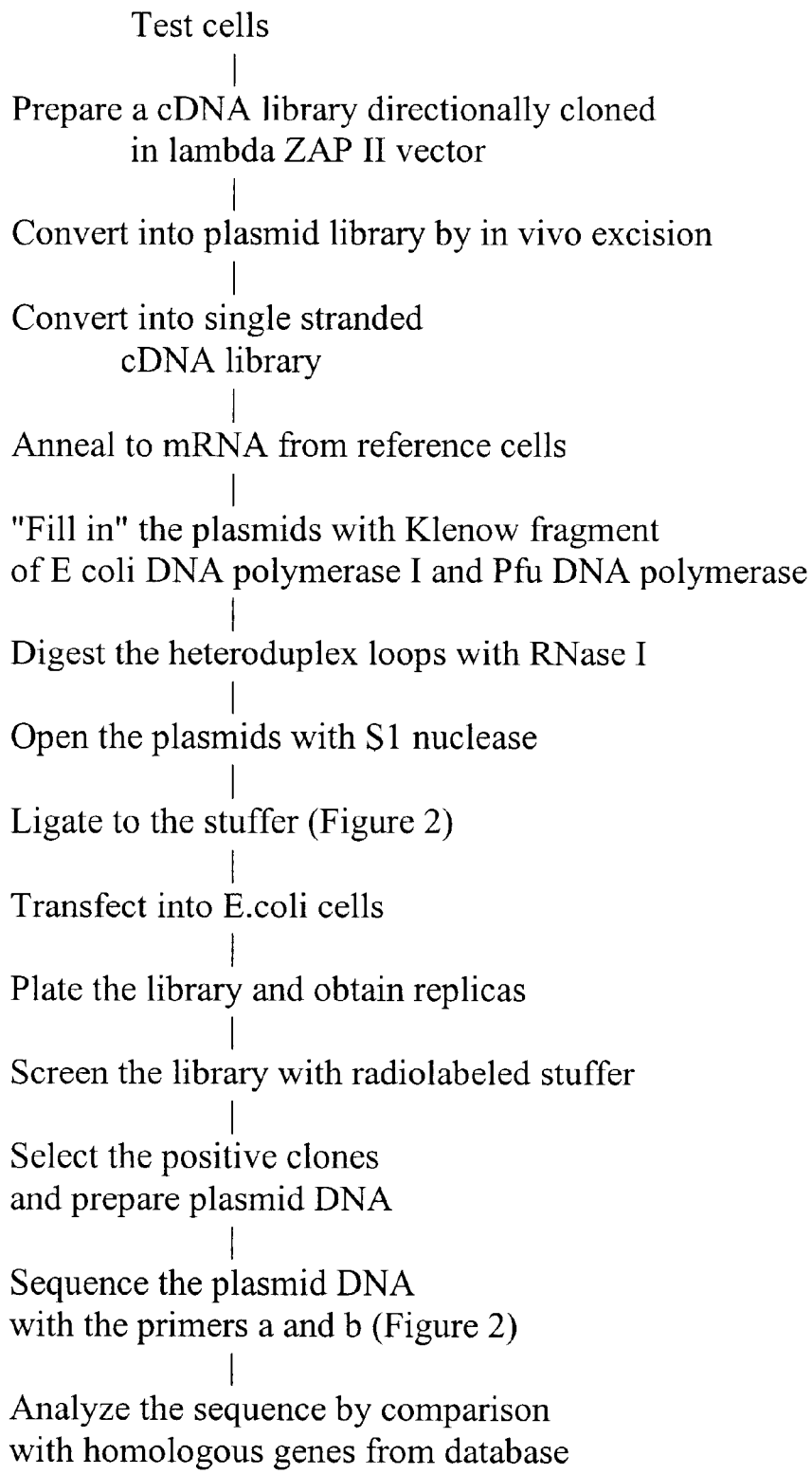

Orita, M., Y. Suzuki, T. Sekiya, and K. Hayashi. 1989. Rapid and sensitive detection of point mutations and DNA polymorphism's using the polymerase chain reaction. Genomics 5:874–879.

Saiki, R.K., S.Scharf, F. Faloona, K.B. Mullis, H.A. Erlich, and N. Arnheim. 1985. Enzymatic amplification of b globin genomic sequences and restriction site analysis for diagnosis of sickle cell anemia. Science ; 230:1350–1354.

White, M., M.Carvalho, D. Derse, S.J. O'Brien, and M. Dean. 1992. Detecting single base mutations as heteroduplex polymorphisms. Genomics; 12:301–306.

Youil, R., J.W. Kemper, and R.G.H. Cotton. 1995. Screening for mutations by enzyme mismatch cleavage with T4 endonuclease. Proc. Natl. Acad. Sci. 92:87–91.

* cited by examiner

```
                        a
         5'- CTATAGTGTCACCTAAATA-3'  (SEQ ID NO. 1)
                           MluI              NruI
                    |       |         |       |                              (SEQ ID NO. 2)
         GGGTTTTCTATAGTGTCACCTAAATAACGCGTCGACGTCGCGATCCCTTTAGTGAGGGTTAATGGGTTTT
         CCCAAAAGATATCACTGTGGATTTATTGCGCTGCTGCAGCGCTAGGGAAATCACTCCCAATTACCCAAAA
                                                                             (SEQ ID NO. 3)
         3'-GATATCACTGTGGATTTAT-5'                    3'-AGGGAAATCACTCCCAATTA-5'
           SP6 polymerase promoter primer (SEQ ID NO. 12)      b     (SEQ ID NO. 4)
```

Figure 2

ATGTGTGGGGTTTTCTA-STUFFER-AATGGGTTTTGATTGAAGCT (SEQ ID NO. 5)

|  |  |
|---|---|
| Sequence obtained by SDBC: | Ile Cys    Ile Glu Ala (SEQ ID NO. 6)<br>ATG TGT G-G ATT GAA GCT (SEQ ID NO. 7) |
| Sequence obtained by RT PCR from MCF7 cells: | Ile Cys Val Ile Glu Ala (SEQ ID NO. 8)<br>ATG TGT GTG ATT GAA GCT (SEQ ID No. 9) |
| Sequence obtained by RT PCR from normal breast cells: | Ile Cys Glu Ile Glu Ala (SEQ ID NO. 10)<br>ATG TGT GAG ATT GAA GCT (SEQ ID NO. 11) |

Figure 3

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
ctatagtgtc acctaaata                                                    19

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence:
      Example of 'Stuffer' Sequence asdescribed in the Specification

<400> SEQUENCE: 2
gggttttcta tagtgtcacc taaataacgc gtcgacgtcg cgatcccttt agtgagggtt      60
aatgggtttt                                                             70

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence:
      Example of 'Stuffer' Sequence as described in the Specification

<400> SEQUENCE: 3 aaacccatt aaccctcact aaagggatcg cgacgtcgac gcgttattta ggtgacacta       60
tagaaaaccc                                                             70

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
attaaccctc actaaaggga                                                  20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: First
      part of 'Stuffer' with ligating ends

<400> SEQUENCE: 5
atgtgtgggg ttttcta                                                     17

<210> SEQ ID NO 6
<211> LENGTH: 6
<212> TYPE: PRT
<213> ORGANISM: Homo sapiens
<220> FEATURE:
<221> NAME/KEY: misc_feature
<222> LOCATION: (3)..(3)

<223> OTHER INFORMATION: Xaa = Glu, Val, Gly, or Ala

<400> SEQUENCE: 6

Ile Cys Xaa Ile Glu Ala
1               5

<210> SEQ ID NO 7
<211> LENGTH: 18
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n = a, t, c, or g

<400> SEQUENCE: 7
atgtgtgnga ttgaagct                                                 18

<210> SEQ ID NO 8
<211> LENGTH: 6
<212> TYPE: PRT
<213> ORGANISM: Homo sapiens

<400> SEQUENCE: 8

Ile Cys Val Ile Glu Ala
1               5

<210> SEQ ID NO 9
<211> LENGTH: 18
<212> TYPE: DNA
<213> ORGANISM: Homo sapiens

<400> SEQUENCE: 9
atgtgtgtga ttgaagct                                                 18

<210> SEQ ID NO 10
<211> LENGTH: 6
<212> TYPE: PRT
<213> ORGANISM: Homo sapiens

<400> SEQUENCE: 10

Ile Cys Glu Ile Glu Ala
1               5

<210> SEQ ID NO 11
<211> LENGTH: 18
<212> TYPE: DNA
<213> ORGANISM: Homo sapiens

<400> SEQUENCE: 11
atgtgtgaga ttgaagct                                                 18

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 12
tatttaggtg tcactatag                                                19

<210> SEQ ID NO 13
<211> LENGTH: 20
<212> TYPE: DNA

```
-continued

<213> ORGANISM: Artificial Sequence
<220> FEATURE:
<223> OTHER INFORMATION: Description of Artificial Sequence: Last
      part of 'Stuffer' with ligating ends

<400> SEQUENCE: 13
aatgggtttt gattgaagct                                              20
```

METHOD OF SIMULTANEOUS DETECTION OF BASE CHANGES (SDBC) IN EXPRESSED GENES

This application claims the benefit of Provisional application Serial No. 60/190,879, filed Mar. 21, 2000 and Provisional application Serial No. 60/266,191, filed Feb. 2, 2001, both of which are hereby incorporated by reference in their entireties.

TABLE OF CONTENTS
1. FIELD OF THE INVENTION
2. BACKGROUND OF THE INVENTION
   1. METHODS BASED ON CHANGES OF ELECTROPHORETIC MOBILITY
   2. MISMATCH CLEAVAGE METHODS
   3. MISMATCH RECOGNITION METHODS
   4. SEQUENCING METHODS
3. SUMMARY OF THE INVENTION
4. BRIEF DESCRIPTION OF THE FIGURES
5. DETAILED DESCRIPTION OF THE INVENTION
   Potential applications of SDBC method
      a. The construction of a cDNA library from cancer cells in lambda ZAP II vector and the generation of the single stranded (ss) phagemid library
      b. Hybridization of ss cDNA library to normal poly (A)+hu + RNA and the conversion into double strand plasmid DNA
      c. Opening the loops from RNA-DNA duplexes
      d. Ligation to stuffer and screening for mutated genes
      e. Determination of the base changes site
6. EXAMPLES
   6.1 Simultaneous Detection of Base Changes
   6.2 Identification of cancer associated SNPs
      a. The preparation of the probes for genes carrying base substitutions
      b. Identification of the subpool of common SNPs

1. FIELD OF THE INVENTION

The present invention relates to methods for detecting polymorphisms in a nucleic acid sample without knowing the nucleotide sequence near the polymorphism. The invention further relates to a method for identifying polymorphisms that are specific for a particular tumor type.

2. BACKGROUND OF THE INVENTION

During the past few decades it has become clear that many human diseases are caused by alterations of cellular proteins, the molecules responsible for carrying out almost all cellular processes. Frequently, these alterations are the consequence of base changes in the nucleotide sequence encoding these cellular proteins. There are two common types of alterations: polymorphisms and mutations.

In humans, it is estimated that there is one base variation every 1–2 kb of homologous chromosomal sequence of any two individuals (Cooper et al. 1985; Kwok et al. 1994). Most of these variations, or polymorphisms, occur in noncoding sequence of the genome and do not alter the observed phenotype. However, some of them occur in the coding sequence and may result in the changes of the biological activity of the proteins they encode. The majority of these polymorphisms are compensated for by the organism, but some of them may lead to disease.

Mutations, however, are molecular alterations which may lead to abnormal protein function which can have serious consequences for the organism. Genetic mutations may be inherited or acquired during an organism's lifetime. Mutations may accumulate spontaneously or are induced by a variety of environmental physical and chemical agents. Organisms are subjected to nearly constant aggression by environmental agents. To prevent a rapid accumulation of multiple mutations and possible cell death, cells rely on DNA repair mechanisms able to correct these environmentally induced mutations. Occasionally, the repair mechanisms fail, and mutations persist leading to cell damage and/or death. If the accumulated mutations are not lethal, they may be transmitted to daughter cells causing genetic disorders in that or future generations.

Cancer may result from accumulation of mutations in multiple genes in one cell or its descendants. Often these mutations lead to the loss of ability to differentiate, to undergo apoptosis or to contact inhibition. The mutations may also lead to uncontrolled proliferation, the enhanced ability for invading surrounding tissues or for metastasizing.

More recently, as the risks for developing different diseases are extensively studied, it appears that variations in the structure of molecules responsible for a cell's handling and response to various agents may determine the propensity of an individual organism to develop a certain disease. The particular handling of an environmental agent will determine ultimately whether or not the agent will have any damaging effect on cell molecules. Thus the individual molecular profile at the level of DNA, RNA and cellular proteins may hold the key to understanding both the risk and the capacity of an individual organism for developing various diseases including cancer.

The determination of this individual molecular profile, that is the subtle differences in the structure of cellular molecules between organisms of the same species, is a task of considerable magnitude. Although there is a large amount of information accumulated during the past few decades regarding various mutations and polymorphisms in numerous genes, the progress towards achieving this objective is rather slow considering the magnitude of the task. This progress is dependent of our ability to detect efficiently and accurately base changes in most and perhaps in all cellular genes.

The existing methods for detection of base changes (Myers et al. 1998) can be broadly divided in the following groups:

1. Methods Based on Changes of Electrophoretic Mobility:

restriction enzyme finger printing (REF)
   denaturing gradient gel electrophoresis (DGGE)
   constant denaturing gel electrophoresis (CDGE)
   carbodiimide mismatch detection
   nondenaturing gel mismatch detection
   single stranded conformational polymorphism (SSCP)

Restriction endonuclease fingerprinting (REF) (Liu and Sommers, 1995) is based on the change of the recognition site for restriction enzymes due a base alteration. This is detected as a change in the size of the DNA fragments generated by the endonuclease when the test and reference DNA are analyzed in parallel in a Southern blot for restriction fragment length polymorphism (RFLP).

Some methods are based on the change of the melting pattern of various DNA domains during the transition from single to double stranded form due to the presence of a base substitution in the sequence. The change in the melting pattern of a DNA fragment can be detected by electrophoresis in denaturing gradient gels (DGGE; Fisher and Lerman 1983), in denaturing constant gels (CDGE; Boresen et al. 1991) or by denaturing high performance liquid chromatography (dHCPL; Oefner unpublished). Using heteroduplexes between mutated and wild type DNA sequences one can also detect base changes by electrophoresis in nondenaturing gels (White et al. 1992). The change in mobility can be enhanced by the attachment at the site of mismatched bases, of a chemical moiety such as carbodiimide (Novack et al. 1986).

Other methods rely on the change of the electrophoretic mobility in nondenaturing gels of a single stranded DNA fragment due to the presence of a base change in the sequence (SSCP; Orita et al. 1989). At present single stranded conformational polymorphism (SSCP) is the most widely used method for detection of base changes. It implies the amplification by RT-PCR of 200–300 bp gene fragment containing the base alteration. The PCR fragment is then subjected to electrophoresis in a nondenaturing polyacrylamide gel including 5–10% glycerol, along with the homologous fragment from the wild type gene. A difference in mobility between the two fragments indicates the presence of a mutation in the target fragment which is then confirmed by sequencing. This method requires the knowledge of the nucleotide sequence of the mutated gene and the approximate location of the mutation so that appropriate PCR primers could be selected for amplification of the target fragment.

2. Mismatch Cleavage Methods:

RNase A cleavage chemical cleavage of mismatches (CCM)

bacteriophage T4 endonuclease 7 cleavage at mismatches (ECM)

mismatch repair enzyme cleavage with *E. coli* Mut Y protein (MREC)

These methods are based on the cleavage of the single stranded RNA or DNA at the site of mismatched bases in heteroduplexes formed between the complementary strands from a reference and a test sample. The method of cleavage could be the digestion with RNase A (Myers et al. 1985), a chemical reaction (CCM; Cotton et al. 1988), or digestion with bacteriophage T4 endonuclease VII (ECM; Youil et al. 1995) or with *E. coli* MutY protein (MREC; Lu and Hsu 1991).

3. Mismatch Recognition Methods:

mismatch repair detection (MRD)

oligonucleotide array hybridization method ("DNA chips")

Mismatch repair detection (MRD, Faham and Cox 1996) identifies base changes by means of a bacterial colony assay based on the mismatched repair system of *E. coli*. A recent promising development in this field is the technique based on DNA hybridization to high density arrays of oligonucleotides ("DNA chips"; Chee et al. 1996; Hacia et al. 1996). These oligonucleotides consist of all possible combinations of a certain number of bases including a specific base change. This method allows the simultaneous detection of a large number of base changes.

4. Sequencing Methods:

These methods detect base changes by direct sequencing of the cloned DNA piece or the fragment obtained by PCR amplification of the region containing base alteration from reference and test cells.

All these methods except those based on DNA chips have 2 major limitations:

they are able to detect base changes only in one gene or in a limited number of genes at a time.

they all require some information about the sequence surrounding the base change.

3. SUMMARY OF THE INVENTION

This invention is directed to a method for detecting base changes in a nucleic acid of interest which comprises the following steps: (a) contacting the nucleic acid of interest with a suitable reference nucleic acid under suitable conditions such that the nucleic acid of interest forms a heteroduplex with the reference nucleic acid; (b) contacting the heteroduplex with a suitable nuclease or a combination of suitable nucleases so as to selectively cleave the heteroduplex if a base change(s) is present; (c) ligating a detectable probe to the cleaved heteroduplex; and (d) detecting the ligated probe under suitable conditions so as determine the location and the sequence of the base changes. In one embodiment, the base change may be a single base change. The nucleic acid of interest may be RNA, it may also be expressed from a cDNA library. The reference nucleic acid may be DNA or a circular nucleic acid.

In one embodiment, the suitable nuclease is S1 nuclease. In another embodiment, the combination of suitable nucleases is both S1 nuclease and RNAase I. The detectable probe may be a nucleic acid.

This invention also includes a kit for detecting single base changes in a nucleic acid of interest which comprises the following components: (a) a suitable reference nucleic acid capable of forming a heteroduplex with the nucleic acid of interest; (b) one or a combination of suitable nucleases capable of selectively cleaving the heteroduplex if a single base change is present; (c) a detectable probe capable of being ligated to the cleaved heteroduplex; and (d) a detecting means for the ligated probe so as determine the location and the sequence of the single base change.

The invention further provides methods for identifying cancer specific polymorphisms. This method encompasses:

a. preparing at least first, second and third replicas from plates generated by plating a first cDNA library prepared from mRNA extracted from cells of a tumor type from a first patient, said plates containing library clones;

b. preparing a first probe by
  i. contacting single stranded nucleic acids from a second cDNA library prepared from mRNA from cells of said tumor type from a second patient with substantially complementary (i.e., complementary except for the polymorphisms to be detected) single stranded nucleic acids from non-tumor cells of the same tissue type of the tumor type under suitable conditions such that the single stranded nucleic acids from the second cDNA library form heteroduplexes with the substantially complementary single stranded nucleic acids from the non-tumor cells;
  ii. contacting the heteroduplexes with a combination of suitable nucleases so as to selectively cleave the heteroduplex where a base change is present;
  iii. ligating a stuffer sequence to the cleaved heteroduplexes to generate stuffer sequence containing clones;
  iv. generating said first probe selectively from those stuffer sequence containing clones, which first probe comprises nucleic acid sequence corresponding to the single stranded nucleic acids;

c. repeating step b to generate at least a second probe generated from single stranded nucleic acids from a third cDNA library prepared from mRNA from cells of said tumor type from a third patient;

d. hybridizing said first and second probes to said first and second replicas;

e. hybridizing the stuffer sequence to said third replica; and f. detecting hybridization of said first and second probes to library clones on said first and second replicas and of said stuffer sequence to clones on said third replica;

wherein library clones that hybridize to the stuffer sequence and to said first and second probes contain cancer associated polymorphisms.

4. BRIEF DESCRIPTION OF THE FIGURES

FIG. 1. FIG. 1 provides a flowchart for the method for simultaneous detection of base changes (SBDC) in expressed genes.

FIG. 2. FIG. 2 provides an exemplary stuffer sequence and sequencing primers a and b and SP6 promoter primer for use in SDBC.

FIG. 3. FIG. 3 provides the sequence of alpha proprionyl CoA carboxylase obtained by the SDBC method from the normal breast and MCF-7 cells.

5. DETAILED DESCRIPTION OF THE INVENTION

This invention is directed to a method for detecting base changes in a nucleic acid of interest which comprises the following steps: (a) contacting the nucleic acid of interest with a suitable reference nucleic acid under suitable conditions such that the nucleic acid of interest forms a heteroduplex with the reference nucleic acid; (b) contacting the heteroduplex with a suitable nuclease or a combination of suitable nucleases so as to selectively cleave the heteroduplex if a base change(s) is present; (c) ligating a detectable probe to the cleaved heteroduplex; and (d) detecting the ligated probe under suitable conditions so as determine the location and the sequence of the base changes. In one embodiment, the base change may be a single base change. In other embodiments, the method detects substitution, insertion or deletion of 2 or more nucleotides, for example, 3 or more, 5 or more, 10 or more, nucleotides. The nucleic acid of interest may be RNA, preferably mRNA (i.e., isolated poly $A^+$ RNA), it may also be expressed from a cDNA library as RNA, or derived by any other method of generating RNA from a DNA source. The reference nucleic acid may be DNA or a circular nucleic acid.

In one embodiment, the suitable nuclease is S1 nuclease. In another embodiment, the combination of suitable nucleases is both S1 nuclease and RNAase I. The detectable probe may be a nucleic acid.

This invention also includes a kit for detecting single base changes in a nucleic acid of interest which comprises the following components: (a) a suitable reference nucleic acid capable of forming a heteroduplex with the nucleic acid of interest (i.e., containing sequences complementary to the nucleic acid of interest except for the base changes to be detected; in certain cases, the reference nucleic acid will contain other nucleic acids not complementary to the nucleic acid of interest); (b) a suitable nuclease or a combination of suitable nucleases capable of selectively cleaving the heteroduplex if a single base change is present; (c) a detectable probe capable of being ligated to the cleaved heteroduplex; and (d) a detecting means for the ligated probe so as determine the location and the sequence of the single base change.

This invention is directed to a method for the identification of base variation in one or more expressed genes in test cells in comparison with these one or more witnessed genes in reference cells. The method is named Simultaneous Detection of Base Changes (SDBC) and relies on a novel procedure of detection of base changes: the insertion of a DNA fragment with a definite sequence at the site of enzymatic cleavage of mismatches in RNA/DNA duplexes. This procedure allows simultaneous detection of base changes in all expressed genes from a cDNA library.

The main steps of an example of SDBC method are shown in FIG. 1. A cDNA library from the test cells is prepared and cloned unidirectionally in lambda ZAP II vector (Stratagene, La Jolla Calif.) (although any library vector can be adapted to the method by one skilled in the art, preferably the library can be converted to single stranded DNA). The library is then converted to single stranded DNA by in vivo mass excision and the use of helper phage. The single stranded clones are hybridized to mRNA from reference cells (or RNA transcribed from a cDNA library) followed by "filling in" the remaining single stranded DNA on the library plasmid (i.e., sequences that do not hybridize to the mRNA, such as vector sequences). This plasmid library is treated with RNase I which opens the RNA strand and then with S1 nuclease which digests the DNA strand at the site of nucleotide mismatches (FIG. 1). Since the digestion of RNA/DNA hybrids is carried out in the cDNA cloned in a plasmid vector this treatment linearizes the plasmid DNA. A DNA fragment with defined sequence ("stuffer") (FIG. 2, by way of example) is ligated to these plasmid clones resulting in their recircularization. The stuffer sequence can be any sequence that has ends capable of ligating to the cleaved plasmid DNA. Preferably, the stuffer also contains restriction enzyme sites for restriction enzymes that cut infrequently (i.e., that are unlikely to be present in the nucleic acid being analyzed) and are not present in the multiple cloning region of the library vector to permit remove of multiple stuffer sequences. Optionally, the stuffer sequence also contains a bacteriophage promoter sequence, for example, an SP6, T7 or T3 promoter sequence. The stuffer sequence should be large enough to accommodate sequencing primers positioned to readily sequence the junction of the stuffer and the clone but small enough such that the plasmid carrying the nucleic acid of interest can also accommodate the stuffer sequence. Preferably, the stuffer sequence is 50 to 100 base pairs, in other embodiments, at least 60, 70, 80, 100, 120, or 150 base pairs and, in other embodiments, no more than 150, 200, 250, 300, 500 or 1000 base pairs.

The recombinant DNA is transfected into E. coli cells (or any other appropriate host), plated and the new library is screened with a suitably labeled stuffer probe. Only cDNA clones containing base changes are cleaved by RNase I/S1 nuclease digestion and have the stuffer inserted into their sequence. Accordingly, these clones can be identified by hybridization to the stuffer sequence. In a specific embodiment plasmids or clones containing the stuffer DNA can be selected or isolated, e.g., by including biotin on one or more residues of the stuffer sequence and after ligation of the stuffer sequence into the linearized plasmids, separation of those plasmids containing the biotinylated stuffer sequence, for example using a streptavidin-conjugated bead column to which the biotin moieties bind, from plasmids not containing the biotinylated stuffer sequence. The population of plasmids thereby enriched for the stuffer sequence can then be amplified by transformation into E. coli and plating to identify and analyze individual clones.

The positive clones are then sequenced with the primers a) and b) (FIG. 2 (for example, SEQ. ID. NOS. 1 and 4, respectively)) located at each end of the stuffer. The sequences generated from these primers are long enough to allow the identification of the site of stuffer insertion into the plasmids. This is the site of base change and its recognition is facilitated by the stretches of GGGTTTT located at the stuffer extremities. The stuffer includes also restriction sites for the rare cutting endonucleases Mlu I and Nru I, not included in the plasmid multiple cloning region (MCR). These endonucleases allow elimination of multiple stuffers which occasionally could be inserted into the same plasmid, which interfere with its sequencing. The sequence generated from the stuffer primers includes also 200–300 nucleotides from the mutated genes sufficient for their identification in database. To confirm the base change, two PCR primers can be selected to selectively amplify the putative mutated gene identified by SDBC and a DNA fragment including the site of base change can be generated by RT-PCR from test cell total RNA. The presence and the location of the putative base alteration can be then confirmed by comparing the base change detected by SDBC method and by RT-PCR.

The invention provides an innovative combination of steps in a novel strategy for detection of base variation:

1. The present method uses RNase I which cuts after all four nucleotides and therefore can detect base changes in any position. A similar cleavage procedure was used before by Myers el al. (1985) who digested RNA at the site of mismatches with RNase A. This enzyme however digests single stranded RNA only after uridine and cytosine. Therefore the rate of mutation detection with Myers' method was only 60% when both complementary RNA strands are analyzed. Another drawback of Myers' method is its inability to screen sequences longer than 1 kb at a time because of unacceptably high background due to RNase A digestion at perfectly matched bases.

Any other enzyme or chemical reaction resulting in specific hydrolysis of RNA/DNA or DNA/DNA duplexes at the level of single nucleotide mismatches can be used in SDBC method.

2. At the site of a base change, a small DNA fragment of defined sequence ("the stuffer") is inserted by ligation. Use of the stuffer fragment allows easy identification of the genes containing putative base changes by hybridization to this fragment. Any DNA fragment of any length or sequence which can be unequivocally recognizable by hybridization or any other procedure to detect linearization of the plasmid can be used instead of the proposed stuffer as discussed above. The stuffer can also be replaced with any protein, hydrocarbonate, prosthetic group, piece of plastic etc., which can be recognized unequivocally. The stuffer may also be a nucleic acid conjugated to a detectable moiety such as biotin which permits ready detection and/or separation of clones containing the stuffer.

3. The digestion at the base change site in the SDBC method is performed in DNA cloned into a plasmid vector. This allows the insertion of the detectable DNA fragment at the base change site and the subsequent detection of individual base changes in a whole library.

Other advantages of the proposed method over the existing methods include:

4. Existing methods require some information about the position of base change in a gene so that the DNA surrounding the base alteration can be PCR amplified or a primer overlapping the base change can be selected. The SDBC method detects base changes in any location in the gene sequence and the sequence surrounding the base change does not need to be known prior to detection.

5. All other existing methods for base change detection require prior knowledge of gene sequence from which convenient primers for PCR amplification can be selected. SDBC method does not require any sequence knowledge for base change detection. Thus, this method can detect base changes in yet unknown locations solely on the presence of a base alteration in their sequence. These genes or the position within the genes can be then identified from GenBank based on the sequence obtained by SDBC method.

Potential Applications of SDBC Method.

a. This method may be used to detect the base changes in expressed genes, including single base changes resulting from the deletion or insertion of one nucleotide or the deletion or insertion of DNA fragments of any size in any gene location.

b. SDBC can also be used to detect base changes in any type of cell from which mRNA can be extracted. These include but are not limited to eukaryotic, prokaryotic, plant cells, etc.

c. By using cells in different stages of development, differentiation, malignant transformation etc. and appropriate reference cells, it is possible to detect base changes underlying the transition from one cell phenotype to another, for example, detecting base changes associated with a particular disease or disorder, developmental process, etc.

d. SDBC can also be used to detect changes in a specific gene or a family of genes by screening the positive clones with a second probe specific for that gene or for the gene family.

e. Since the knowledge of the sequence is not required for detection of base changes, the SDBC method can be used to identify novel genes altered in various processes.

f. The method can also be used to detect base changes in expressed genes after treatment in vivo or in vitro of cells or of whole organisms with physical (X rays, UV irradiation, atomic particle bombardment, etc), chemical (drugs, various compounds, biological products, etc.), or biological (viruses, bacteria, etc.) agents.

g. SDBC can be used to detect polymorphic differences among individuals, for example, in determining paternity, assessing the risk for certain diseases, forensic analysis, etc.

h. SDBC may also be used to study the DNA variation in the process of maturation, aging, etc.

The major steps in one embodiment of the SDBC method are summarized here. Most of the techniques used in this method are standard procedures in the art. Those skilled in the art would be able to modify the method based upon basic molecular biological techniques. A preferred protocol is described in detail below.

a. The Construction of a cDNA Library from Cancer Cells in Lambda ZAP II Vector and the Generation of the Single Stranded (ss) Phagemid Library.

A cDNA library from test cells is unidirectionally cloned in lambda ZAP II vector (Stratagene, La Jolla Calif.) or in any other vector for suitable direct subcloning in plasmids. This cDNA library is subcloned into pBluescript plasmid by in vivo mass excision and then converted into single stranded plasmid library using ExAssist helper phage (Stratagene, La Jolla Calif.). This plasmid library should contain the minus strands of cDNA clones.

b. Hybridization of ss cDNA Library to Normal Poly (A)$^+$ RNA and the Conversion into Double Strand Plasmid DNA.

The single stranded (ss) plasmid library generated in step a is hybridized to an excess of poly (A)$^+$ RNA extracted from reference cells.

The remaining ss plasmid DNA (i.e., the plasmid DNA portion not hybridized to RNA) is then converted into double stranded (ds) DNA by "filling" in the single stranded DNA with random primers, dNTPs and the Klenow (large) fragment of E. coli DNA polymerase. There are other alternatives to Klenow fragment treatment like T4 DNA polymerase, T7 DNA polymerase (SEQUENASE™) or thermostable Pfu DNA polymerase or any other method known in the art for filling in single-stranded nucleic acid. Pfu DNA polymerase is preferred because of its low error rate of nucleotide incorporation, reducing the incidence of nucleotide mismatches in the newly synthesized ds DNA. Since this polymerase does not extend RNA primers, the filling reaction should be initiated with Klenow fragment for the first 5 minutes and then the incubation should be continued at 72° C. for 60 minutes to inactive Klenow fragment and to allow the Pfu polymerase to fill in the ds plasmid DNA. The gaps between the newly synthesized DNA and the RNA strands are sealed with E coli and T4 DNA ligase.

c. Opening the Loops from RNA-DNA Duplexes.

The loops resulting from the mismatched nucleotides at the sites of base variation in the RNA/DNA duplexes are cleaved by treatment first with RNase I (Meador et al. 1990), which digests the RNA strand, followed by incubation with S1 nuclease which hydrolyzes the DNA strand at the site of the gap created by digestion with RNase I. These enzymes under appropriate conditions digest preferentially single stranded RNA and DNA. However, any nuclease or combination of nucleases suitable for cleaving such an RNA-DNA loop may be used.

After this step, the clones containing base changes become linear, while the cDNA clones without base alterations remain double stranded circular DNA.

d. Ligation to Stuffer and Screening for Mutated Genes.

The RNA strand from the heteroduplexes is replaced with homologous DNA sequences by treatment with RNase H and E. coli polymerase in the presence of dNTP. The linear double stranded plasmid DNA is then made blunt ended, diluted to 2 ng/µl and then ligated in high molar excess to blunt ended stuffer (FIG. 2) to ensure that all linearized plasmids are circularized by insertion of the stuffer. This stuffer is a 70 bp double stranded DNA fragment (See FIG. 2; SEQ ID NOS. 2 and 3). The stuffer can be prepared from single stranded primers using methods well known in the art.

Following stuffer ligation and circularization, the recombinant plasmid DNA is transfected into E. coli cells, plated and replicated. The replicas are then screened with the stuffer end labeled with gamma $^{32}$P ATP and T4 polynucleotide kinase. The positive clones are selected, miniprep plasmid DNA prepared and sequenced with the primers a) and b) (FIG. 2; SEQ ID NOS. 1 and 4, respectively), and the site of stuffer/insert connection determined. This is the site of putative base change.

e. Determination of the Base Changes Site.

The sequences generated from the stuffer primers should include 20–30 nucleotides from stuffer sequence, the site of stuffer insertion and at least 300–400 nucleotides from the mutated clones which is usually sufficient for the gene identification in a database. The location of stuffer insertion in the cDNA clone indicates the site of digestion with RNase I and S1 nuclease and the position of putative base change. The base change should be then confirmed by RT-PCR from test and reference cells using standard techniques.

The following changes to the SDBC method are also included herein:

1. The construction of the initial cDNA library directly into a phagemid instead of a phage vector. By using electroporation of bacterial cells, it is possible to obtain high efficiency transformation in the range of 0.5–1×10$^9$ transformants/µg DNA sufficient for preparation of a cDNA library.

2. Normalization of the cDNA library before screening with the stuffer probe using methods well known in the art. In this way the low and high abundance clones will have a similar chance of base detection.

3. The digestion of the recombinant cDNA library containing the stuffer-sequence containing clones before transformation into bacterial cells with Mlu I or Nru I endonucleases (or whatever restriction endonuclease sites are included in the stuffer sequence) followed by re-ligation and bacterial transformation. The positive clones should contain only one stuffer molecule, thus facilitating sequencing.

4. The selection of clones containing the stuffer by passing the recombinant cDNA after stuffer ligation through an affinity column with covalently bound single stranded stuffer DNA. The eluate from such a column will be markedly enriched in plasmid DNA containing stuffer and potentially base changes. After transfection into E. coli this DNA will produce almost exclusively positive clones.

5. The use of defined mRNA fragments for hybridization to single stranded cDNA clones.

Using overlapping RNA fragments of 200–300 nucleotides instead of the whole gene mRNA, one can detect up to two base changes in each fragment and, in this way, potentially all the base changes in each library clone.

The digestion of mRNA at well defined points can be performed by hybridizing the RNA to short complementary DNA sequences. Then the RNA/DNA hybrids are treated with RNase H which digests the RNA sequence only at the site of RNA/DNA duplexes. RNA digestion at defined points may be performed, for example, using the method of Goodwin and Rottman (1991). Fourmer oligodeoxynucleotides containing the restriction sites of two frequently cutting endonucleases, such as Hae III and Alu I, can be synthesized commercially. Five µg mRNA from reference cells and 5 µg oligomers containing the endonuclease sites will be mixed in 20 µl volume containing 40 mM HEPES (pH 7.9 at 40° C.), 10 mM MgCl$_2$, 60 mM KCl and 1 mM DTT, denatured under oil at 70° C. for 5 minutes and then cooled slowly at 4° C. After adding 2 µg RNase H, the incubation will be continued for 16 hours at 4° C. Next day the DNA oligomers will be digested with 2 U RNase free DNase I for 30 minutes at 37° C., phenol chloroform extracted once, chloroform extracted once and precipitated with 3 volumes of alcohol in the presence of ammonium acetate at −70° C. for 30 minutes. The RNA will be pelleted by centrifugation at 35,000 g for 30 minutes at 4° C. The precipitation with ammonium acetate will be repeated twice to remove most of free nucleotides. The RNA will be then hybridized to single stranded cloned cDNA from test cells prepared as described. Equal amounts of samples prepared with Hae III and Alu I will be mixed and further processed according to SDBC protocol.

The Examples shown below are in no way to be construed as limiting the scope of this invention. One of ordinary skill would readily recognize that many modifications, both to the materials and to the method, may be practiced without departing from the purpose and interest of this invention.

6. EXAMPLES

6.1 Simultaneous Detection of Base Changes

We tested the ability of the SDBC method to detect base variation in mRNA from the MCF-7 breast carcinoma cell line in comparison with mRNA from 48R normal breast epithelial cells both obtained from ATCC. We followed the protocol summarized in FIG. 1. The total RNA from cultured MCF-7 breast carcinoma and 48R normal breast cell lines was prepared by Chomszynski's method (Chomszynski 1987). The quality of RNA was tested by electrophoresis on a 1% formaldehyde gel. The mRNA was prepared using BioMag oligo (dT)20 (Advanced Magnetics Inc., Cambridge, Mass.) and the protocol from manufacturer. The digestion with RNase I, a preferred step in this method, has been tested in our laboratory and the experimental conditions giving the best results were introduced in SDBC protocol.

a. The Construction of a cDNA Library from MCF-7 Cells in Lambda ZAP II Vector and the Generation of the Single Stranded (ss) Phagemid Library.

A cDNA library from MCF-7 cells was unidirectionally cloned into the lambda ZAP II vector (Stratagene, La Jolla Calif.) using the kit of reagents and the manufacturer's protocol. The first cDNA strand was synthesized from 5 μg mRNA, dNTP with methylcytosine instead of cytosine, a linker primer including a poly T sequence and the murine leukemia virus reverse transcriptase, at 37° C. for 1 hour. The second cDNA strand was synthesized with RNase H and DNA polymerase I, at 16° C. for 2½ h. Both cDNA strands were about 1.5–2 kb in size when analyzed by electrophoresis in a 1% alkaline agarose gel. After blunting the cDNA termini with Pfu DNA polymerase at 72° C., the cDNA was ligated to an excess of EcoRI adapters at 4° C., for 2 days. After phosphorylating the Eco RI ends with polynucleotide kinase, the cDNA was digested with Xho I, followed by size fractionation on a Sepharose CL 4B column. Two microliters from each fraction were tested by electrophoresis in a 1% agarose gel and the fractions containing cDNA larger than 0.5 kb were pooled. One hundred nanograms from this cDNA were then ligated to 1 μg lambda ZAP vector, predigested with EcoR I and Xho I and treated with calf intestinal alkaline phosphatase (Stratagene, La Jolla), at 4° C., for 2 days. Then, 2 μl ligation mixture was packaged using Gigapak III Gold packaging extract (Stratagene).

About $10^6$ clones were subjected to one round of amplification on 20 large plates using XL1-Blue MRF' E. coli strain. The phage were collected and stored at 4° C. with 5% chloroform, and at −70° C. as a glycerol stock. This lambda ZAP cDNA library had about $10^{10}$ pfu/ml after preparation. The library was subcloned in pBluescript (pBS) phagemid by in vivo mass excision using RE704 helper phage and then converted into single stranded plasmid library with ExAssist helper phage following the vendor's protocols (Stratagene, La Jolla Calif.). This plasmid library contained the cDNA clones' minus strand.

b. Hybridization of ss cDNA library to normal poly (A)+ RNA and the conversion into double stranded plasmid DNA. For the SDBC method it was particularly important not to have an excess of unhybridized RNA sequences which could interfere with the filling in the next step. Since pBS vector is about 3 kb and the average size of the cDNA clone in the lambda ZAP library was about 1.5 kb, 3 μg cloned cDNA were roughly equimolar with 1 μg mRNA. Therefore, three micrograms of single stranded plasmid cDNA library and 1 μg normal breast mRNA were ethanol precipitated and then resuspended in 30 μl hybridization buffer (80% deionized formamide, 50 mM PIPES pH 6.4, 0.5 M NaCl, 1 mM EDTA), denatured for 10 minutes at 95° C. and incubated under oil, at 55° C., overnight. The (ss) plasmid DNA containing the RNA-cDNA hybrids was then converted into double stranded (ds) DNA by "filling in" with random primers, dNTP, the Klenow fragment of E. coli DNA polymerase and Pfu polymerase. Pfu DNA polymerase was used because it has the lowest rate of nucleotide missincorporation and, therefore, gave the lowest chance for generating false nucleotide mismatches in the newly synthesized (ds) DNA. Since this polymerase does not extend RNA primers, the filling reaction was initiated with Klenow fragment for the first 3 minutes at 16° C., followed by incubation at 72° C., for 30 minutes, conditions which inactivated Klenow fragment and allowed the Pfu polymerase to fill in the ss plasmid DNA. The gaps between the newly synthesized DNA and the RNA strands were sealed with a mixture of E. coli and T4 DNA ligases.

c. Opening the Loops from RNA-DNA Duplexes.

The loops resulting from mismatched nucleotides at the sites of base changes in RNA/DNA duplexes were opened by treatment with RNase I, which digested the RNA strand, followed by incubation with S1 nuclease, which digested the DNA strand at the gap created by digestion with RNase I. These enzymes under appropriate conditions digest preferentially single stranded RNA and DNA.

RNase I is a 27 kD endonuclease which digests RNA with no preference for the type of nucleotide (Meador 1989). It does not degrade DNA and has a marked preference for single stranded RNA. RNase I has been cloned and overexpressed in E. coli and it is available commercially (cat# 1419, Ambion Inc, Austin Tex.).

In the SDBC protocol, two micrograms of plasmid DNA containing RNA/DNA inserts as duplexes were treated with 65 units RNase I (Ambion Inc., Austin, Tex.) in 20 μl volume containing 10 mM Tris.HCl pH 7.5, 5 mM EDTA and 20 mM Na acetate, at 37° C. After 15 minutes, the reaction was stopped by extraction with phenol/chloroform, followed by ethanol precipitation.

For digestion with S1 nuclease, two micrograms of DNA in 50 μl of 1×S1 nuclease buffer (50 mM sodium acetate pH 5.7, 200 mM NaCl, 1 mM ZnSO4, 0.5% glycerol) were warmed at 37° C. for 5 minutes, and then incubated with 3000 units S1 nuclease (Pharmacia Biotech Inc., Piscataway, N.J.) at 37° C. for 20 minutes. After the addition of 2 μl of 50 mM EDTA and 2 μl of 1 mM Tris.HCl pH 7.6, the mixture was extracted with phenol/chloroform, followed by ethanol precipitation. After this step, the clones containing the base changes became linear, while the cDNA clones without base alterations remained double stranded circular DNA.

d. Ligation to Stuffer and Screening for Mutated Genes.

The RNA strands from heteroduplexes were replaced with homologous DNA sequences by treatment with RNase H and Klenow fragment of E. coli polymerase in the presence of dNTP, according to the standard protocol for the second strand cDNA synthesis (Sambrook 1989). The linear double stranded plasmid DNA was made blunt ended with T4 DNA polymerase, diluted and then ligated in high molar excess to blunt ended stuffer, to increase the chances for plasmid circularization by stuffer insertion.

Following the stuffer ligation and circularization, the recombinant plasmid DNA was electroporated into XL1 Blue MRF' E. coli cells and about 100,000 colonies plated and replicated. The replicas were then screened with the stuffer end labeled with gamma $^{32}$P ATP and T4 polynucleotide kinase. The positive clones were selected, miniprep plasmid DNA prepared and sequenced with the primers a) and b) (see FIG. 2, SEQ ID NOS. 1 and 4, respectively), and the site of stuffer/insert connection determined. This was the site of putative base change.

e. Determination of the Base Changes Sites.

The sequences generated from the stuffer primers included 20–25 nucleotide from stuffer sequence, the site of stuffer insertion and about 300–400 nucleotides from the mutated clones sufficient for gene identification in database using Blast program. The location of stuffer insertion in the cDNA clones indicated the site of digestion with RNase I and S1 nuclease and the position of putative base change.

f. Results.

From about 100,000 colonies screened with the radiolabeled stuffer, some 200 positive clones were identified from which three clones were analyzed. Initially, the sequence obtained with either a) or b) primer could not be read. The digestion of the clones with Mlu I generated a small fragment of stuffer size indicating that more than one stuffer had been inserted into the clone. More plasmid DNA was then digested with Mlu I restriction endonuclease and the free stuffers removed. The digested plasmids were religated, transfected into *E. coli*, plated and analyzed. The new clones could be sequenced without difficulty and were shown to contain a single stuffer.

The clone sequences were then compared to homologous sequences from GenBank. The first clone encoded alpha propionyl-CoA carboxylase cDNA and had 2 nucleotides missing at residue # 682 (FIG. 3). The missing nucleotides were most likely removed by digestion with S1 nuclease at the site of the gap created by RNase I digestion.

To confirm the base change two PCR primers were selected from the gene sequence and a DNA fragment containing the base alteration was obtained by RT-PCR amplification of MCF 7 and normal breast cell total RNA. The fragments were sequenced and compared with the sequence obtained from our recombinant library (FIG. 3). The base change detected in propionyl-CoA carboxylate was confirmed to be a true base alteration since it was found in the PCR fragment from cancer cells but not from normal cells. The second clone encoding for p53 cDNA had a base change at nucleotide # 230 in the cDNA library prepared with SDBC method. This base change was also found in a similar fragment amplified by RT-PCR from MCF-7 total RNA but not in RNA from normal breast cells. The third clone encoded for topoisomerase I cDNA; no base change could be confirmed in the DNA fragment obtained by RT-PCR from MCF-7 total RNA. Thus the SDBC method detected correctly 2 out of 3 base changes in MCF-7 cDNA library confirming its ability to identify base substitution as expected.

6.2 Identification of Cancer Associated SNPs

SDBC method as well as the other methods for global detection of base substitutions cannot be used to distinguish the disease associated SNPs from other polymorphisms. This means that a considerable number of genes will be analyzed by sequencing only to find out that they carry polymorphic variations without any relevance for the disease in question.

Here we describe a strategy to identify the cancer associated SNPs from nucleotide substitutions irrelevant to cancer.

The basic concept of this strategy is the following: when several cDNA libraries from the same tumor but from different patients are analyzed against the same reference cDNA library (e.g., from normal cells from the same tissue) two SNP subpools can be identified:

1—a very large subpool of polymorphic changes containing SNPs that differ from one patient to another.

2—a very small subpool of SNPs common to all tumoral cDNA libraries including the mutations in the genes involved in malignant transformation in that tissue. In addition this subpool will probably include very common polymorphisms and those SNPs commonly associated with the risk for the studied malignancy.

As the number of analyzed tumor specimens increases, this subset of common SNPs will become smaller and ultimately will comprise substantially only the SNPs required or associated with that specific malignancy. Once the SNP pool from each cDNA library is determined, the subpool of common SNPs can be determined by computer analysis.

Here we propose a different strategy for identification of the subpool of tumor associated SNPs. This strategy does not require prior identification by sequencing of all SNPs from any tumoral cDNA library. The strategy instead consists of preparation of a probe for all clones carrying the stuffer (i.e., having an SNP) from each tumor cDNA library. Then one cDNA library is plated and the replicas from those plates are screened successively with the probes prepared from the other tumoral libraries. The clones hybridizing to all these probes are the subpool of common SNPs to all tumoral specimens and are most likely tumor associated SNPs.

This strategy is derived from SDBC methodology and can be used only when base variations are identified with this method.

The main steps of this strategy are the following:

a. The Preparation of the Probes for Genes Carrying Base Substitutions.

There are two procedures for preparation of probes for clones containing the stuffer from a cDNA library:

DNA probes can be prepared by PCR amplification of the cDNA sequences between the stuffer and the plasmid vector. The plasmid primer is preferably the SK sequencing primer (Stratagene) included in the vector MCS (or other equivalent primer appropriate for PCR amplification), located close to the EcoRI restriction site where cDNA clones have been inserted in the lambda ZAP II vector. The second PCR primer is the SP6 RNA polymerase promoter primer located at the 5' stuffer extremity (SEQ ID NO. 12, depicted in FIG. 2) of the stuffer sequence or other suitable primer for amplifying the DNA sequence of the clone between the vector and the stuffer sequence. The PCR amplification is performed with the plasmid cDNA library after the stuffer insertion step and following the removal of free stuffers as described above. The DNA generated by PCR with these primers will contain probes specific for clones containing the stuffer since the SP6 primer is found only in the stuffer. The PCR generated will include however the SK primer present on the vector. Therefore, this probe could give a low hybridization background with clones not containing the stuffer sequence if the conditions of hybridization are not stringent enough. However, the probe can specifically identify the subpool of common SNPs (i.e., those clones containing the stuffer sequence) if the appropriate hybridization conditions are used. Such hybridization conditions can be identified using routine methods.

RNA probes can be prepared using SP6 RNA polymerase. The promoter for this polymerase is included in reverse orientation in the stuffer sequence and it is complementary to sequencing primer a (FIG. 2, SEQ ID NO. 1) (alternatively, another promoter, preferably a bacteria or bacteriophage promoter, e.g., T7 or T3 promoter, can be incorporated into the stuffer sequence and the appropriate polymerase (e.g., T7 or T3 polymerase) used to transcribe the probe). In order to ensure the transcription only of the cDNA inserts, the plasmid DNA should be digested first with EcoR I and Xho I (or other appropriate restriction enzyme that will cut at or near the insert/plasmid boundary so that the transcripts will stop at the insert/plasmid boundaries). Since the digestion with these endonucleases may not be always complete even in optimal conditions, the digestion with a second pair of endonucleases like Kpn I and Pst I, with restriction sites outside of Eco R I and Xho I in the vector MCS, should be also performed. After endonuclease digestion, the DNA will be phenol and then phenol chloroform extracted and ethanol precipitated under RNase free conditions. The transcription of the inserts will be performed with SP6 RNA polymerase and a kit of reagents from Ambion Comp (or any other reagents standard for SP6 polymerase transcription) followed by DNA template digestion with DNase I. These transcripts should be specific only to the inserts containing the stuffer and should not give any background hybridization since they do not have any sequence homology with the vector or stuffer.

For preparation of both DNA and RNA probes, appropriate radioactive tracers or biotinylated nucleotides may be incorporated at the time of synthesis.

b. Identification of the Subpool of Common SNPs.

For this purpose at least three recombinant cDNA libraries from three different patients will be obtained and stuffer sequences inserted at polymorphisms using the SDBC method. Then a cDNA library from one patient will be plated and three replicas from each plate will be obtained. One replica will be hybridized to the stuffer probe and the other two to the probes prepared from the other two tumors. The colonies hybridizing to all three probes are the clones containing SNPs (because they hybridize to stuffer probe) and are also common to all three malignancies. Only these clones will be analyzed by sequencing.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

REFERENCES

Borresen, A. L., E. Hove, B. Smith-Sorenssen, D. Malkin, S. Lystad, T. I. Andersen, J. M. Nesland, K. H. Isselbacher, and S. H. Friend. 1991. Constant denaturant gel electrophoresis as a rapid screening technique for p53 mutations. Proc. Natl. Acad. Sci. 88:8405–8409.

Chee, M., R. Yang, E. Hubbell, A. Berno, S. C. Huang, D. Stern, J. Winkler, D. J. Lockhart, M. S. Morris, and S. P. Fodor. 1996. Accessing genetic information with high density DNA arrays. Science 274: 610–614.

Chomszynski, P., and Sacchi, N., 1987. Single step method of RNA isolation by acid guanidinium thiocyanate phenol chloroform extraction. Anal. Biochem. 162: 156–159

Cotton, R. G., N. R. Rodriguez, and Campbell. 1988. Reactivity of cytosine and thymine in single base pair mismatches with hydroxylamine and osmium tetroxide and its application to the study of mutations. Proc. Natl. Acad. Sci. 85:4397–4401.

Cooper, D. N., B. A. Smith, H. J. Cooke, S. Niemann, and J. Schmidtke. 1985 An estimate of unique DNA sequence heterozygosity in the human genome. Hum. Genet. 69: 201–295.

Donis-Keller H. 1979. Site specific enzymatic cleavage of RNA. Nucl. Acids Res. 7: 179–192.

Faham, M., and D. R. Cox. 1996. A novel in vivo method to detect DNA sequence variation. Genome Res. 5: 474–482.

Fisher, S. G., and L. S. Lerman. 1983. DNA fragments differing by single base pair substitutions are separated in denaturing gradient gels. Correspondence with melting theory. Proc. Natl. Acad. Sci. 80: 1579–1583.

Goodwin E. C. and F. M. Rottman 1991. The use of Rnase H and poly(A) junction oligonucleotides in the analysis of in vitro polyadenylation reaction products. Nucl. Acids Res. 20: 916.

Kwok, P. Y., C. Carlson, T. D. Yager, W. Ankener, and D. A. Nickerson. 1994. Comparative analysis of human DNA variations by fluorescence based sequencing of PCR products. Genomics 23: 138–144

Liu, Q. and S. S. Sommer. 1995. Restriction endonuclease fingerprinting (REF): A sensitive method for screening mutations in long, contiguous segments of DNA. Bio-Techniques 18:470–477.

Lu, A.-L. and I. C Hsu. 1991. Detection of single DNA base mutations with mismatch repair enzymes. Genomics 14:249–255.

Meador J., B. Cannon, V. J. Cannistraro and D. Kennell 1989. Purification and characterization of E. coli Rnase I. Eur. J. Biochem., 187: 549–543

Mullis, K., F. Faloona, S. Scharf, R. Saiki, G. Horn, and H. Erlich. 1986. Specific enzymatic amplification of DNA in vitro: The polymerase chain reaction. Cold Spring Harbour Symp. Quant. Biol. 51:263–273.

Myers, R. M., Z. Larin, and T. Maniatis. 1985. Detection of single base substitutions by ribonuclease cleavage of mismatches in RNA:DNA duplexes. Science 230:1242–1246.

Myers, R. M., Ellenson L. H. and K. Hayashy. Detection of DNA variation in Genome Analysis, Cold Spring Laboratories Press, vol.2, pg. 287–379.

Novack, D. F., N. J. Casna, S. G. Fischer, and J. P. Ford. 1986. Detection of single base pair mismatches in DNA by chemical modification followed by electrophoresis in 15% polyacrylamide gel. Proc. Natl. Acad. Sci. 83:586–590.

Orita, M., Y. Suzuki, T. Sekiya, and K. Hayashi. 1989. Rapid and sensitive detection of point mutations and DNA polymorphism's using the polymerase chain reaction. Genomics 5:874–879.

Saiki, R. K., S. Scharf, F. Faloona, K. B. Mullis, H. A. Erlich, and N. Arnheim. 1985. Enzymatic amplification of b globin genomic sequences and restriction site analysis for diagnosis of sickle cell anemia. Science; 230:1350–1354.

Sambrook J., Fritsch E F., and Maniatis T. 1989. Molecular Cloning. Alaboratory manual, pg. 15.40

White, M., M. Carvalho, D. Derse, S. J. O'Brien, and M. Dean. 1992. Detecting single base mutations as heteroduplex polymorphisms. Genomics; 12:301–306.

Youil, R., J. W. Kemper, and R. G. H. Cotton. 1995. Screening for mutations by enzyme mismatch cleavage with T4 endonuclease. Proc. Natl. Acad. Sci. 92:87–91.

I claim:

1. A method for detecting base changes in a nucleic acid of interest which comprises the following steps:
    (a) contacting the nucleic acid of interest with a suitable reference nucleic acid under suitable conditions such that the nucleic acid of interest forms a heteroduplex with the reference nucleic acid;
    (b) contacting the heteroduplex with a suitable nuclease or a combination of suitable nucleases so as to selectively cleave the heteroduplex at a position of a base change on the nucleic acid of interest with respect to the reference nucleic acid;
    (c) ligating a DNA fragment with a defined sequence to the cleaved heteroduplex; and
    (d) detecting the ligated DNA fragment under suitable conditions so as to determine the presence and location of the base change.

2. The method claim 1 wherein the base change is a single base change.

3. The method claim 1 wherein the nucleic acid of interest is RNA.

4. The method of claim 3 wherein the RNA is expressed from a cDNA library.

5. The method of claim 1 wherein the reference nucleic acid is DNA.

6. The method of claim 1 wherein the reference nucleic acid is a circular nucleic acid.

7. The method of claim 6 wherein the suitable nuclease is S1 nuclease.

8. The method of claim 6 wherein the combination of suitable nucleases is S1 nuclease and RNAase I.

9. The method of claim 1 wherein the DNA fragment has the sequence set forth in FIG. 2.

10. A kit for detecting base changes in a nucleic acid of interest which comprises the following components:
    (a) a suitable reference nucleic acid capable of forming a heteroduplex with the nucleic acid of interest;
    (b) a suitable nuclease or a combination of suitable nucleases capable of selectively cleaving the heteroduplex at a position of a base change on the nucleic acid of interest with respect to the suitable reference nucleic acid;
    (c) a DNA fragment of defined sequence capable of being ligated to the cleaved heteroduplex; and
    (d) a means to detect the ligated DNA fragment.

11. The kit claim 10 wherein the base change is a single base change.

* * * * *